(12) United States Patent
Yum et al.

(10) Patent No.: US 6,572,879 B1
(45) Date of Patent: Jun. 3, 2003

(54) FORMULATIONS FOR TRANSDERMAL DELIVERY OF PERGOLIDE

(75) Inventors: Su Il Yum, Los Altos, CA (US); Melinda K. Nelson, Sunnyvale, CA (US); Patricia S. Campbell, Palo Alto, CA (US)

(73) Assignee: Alza Corporation, Palo Alto, CA (US)

( * ) Notice: Subject to any disclaimer, the term of this patent is extended or adjusted under 35 U.S.C. 154(b) by 0 days.

(21) Appl. No.: 08/473,631

(22) Filed: Jun. 7, 1995

(51) Int. Cl.⁷ .................. A61M 37/00; A61K 9/70; A61K 31/437; A61P 25/16
(52) U.S. Cl. ................... 424/449; 514/947; 514/288
(58) Field of Search ................. 424/448, 449; 514/947, 288, 410

(56) References Cited

U.S. PATENT DOCUMENTS

| | | | |
|---|---|---|---|
| 3,598,122 A | 8/1971 | Zaffaroni | 128/268 |
| 3,598,123 A | 8/1971 | Zaffaroni | 128/268 |
| 3,731,683 A | 5/1973 | Zaffaroni | 128/268 |
| 3,797,494 A | 3/1974 | Zaffaroni | 128/268 |
| 4,031,894 A | 6/1977 | Urquhart et al. | 128/268 |
| 4,144,317 A | 3/1979 | Higuchi et al. | 424/21 |
| 4,166,182 A | 8/1979 | Kornfeld et al. | 546/67 |
| 4,201,211 A | 5/1980 | Chandrasekaran et al. | 128/268 |
| 4,286,592 A | 9/1981 | Chandrasekaran | 128/260 |
| 4,314,557 A | 2/1982 | Chandrasekaran | 128/260 |
| 4,379,454 A | 4/1983 | Campbell et al. | 604/897 |
| 4,435,180 A | 3/1984 | Leeper | 604/896 |
| 4,559,222 A | 12/1985 | Enscore et al. | 424/28 |
| 4,568,343 A | 2/1986 | Leeper et al. | 604/896 |
| 4,573,995 A | 3/1986 | Cheng et al. | 604/896 |
| 4,588,580 A | 5/1986 | Gale et al. | 424/21 |
| 4,645,502 A | 2/1987 | Gale et al. | 604/896 |
| 4,704,282 A | 11/1987 | Campbell et al. | 424/449 |
| 4,764,379 A | 8/1988 | Saunders et al. | |
| 4,788,062 A | 11/1988 | Gale et al. | 424/449 |
| 4,797,405 A | 1/1989 | Conine et al. | 514/288 |
| 4,800,204 A | 1/1989 | Mueller | 514/267 |
| 4,816,258 A | 3/1989 | Nedberge et al. | 424/448 |
| 4,849,226 A | 7/1989 | Gale | 424/448 |
| 4,908,027 A | 3/1990 | Enscore et al. | 604/890.1 |
| 4,935,429 A | 6/1990 | Deckis et al. | 514/288 |
| 4,943,435 A | 7/1990 | Baker et al. | 424/448 |
| 5,004,610 A | 4/1991 | Osborne et al. | 424/448 |
| 5,063,234 A | 11/1991 | Bryant et al. | 514/288 |
| 5,229,129 A | 7/1993 | Chiang | 424/449 |
| 5,252,335 A | 10/1993 | Chiang | 424/449 |
| 5,314,694 A | 5/1994 | Gale et al. | |
| 5,378,730 A | * 1/1995 | Lee et al. | 514/786 |
| 5,446,070 A | * 8/1995 | Mantelle | 424/488 |
| 5,607,691 A | 3/1997 | Hale et al. | 424/449 |

FOREIGN PATENT DOCUMENTS

| DE | 4240798 A1 | 6/1983 |
|---|---|---|
| EP | 0279986 | 8/1988 |
| EP | 0559411 | 9/1993 |

* cited by examiner

Primary Examiner—Edward J. Webman
(74) Attorney, Agent, or Firm—Vandana Date

(57) ABSTRACT

Composition of matter for application to a body surface or membrane to administer pergolide by permeation through the body surface or membrane, the composition comprising pergolide to be administered, at a therapeutically effective rate, alone or in combination with a permeation enhancer or mixture. Also disclosed are drug delivery devices containing the pergolide or pergolide and enhancer composition and methods for the transdermal administration of the pergolide and pergolide/enhancer composition.

47 Claims, 9 Drawing Sheets

FORMULATIONS FOR TRANSDERMAL DELIVERY OF PERGOLIDE

FIELD OF INVENTION

This invention relates to the safe and efficacious transdermal administration of pergolide for, among other things, the treatment of Parkinson's Disease. More particularly, the invention relates to novel methods, compositions, and devices for administering pergolide to a subject through a body surface or membrane over a sustained time period.

BACKGROUND OF THE INVENTION

Pergolide, 8-[(methylthio)methyl]-6-propylergoline, a compound based on the ergoline ring system, is reported to be a dopaminergic agonist that also decreases plasma prolactin concentrations. When used for treating Parkinson's Disease, pergolide is used as an adjuvant to levodopa.

U.S. Pat. No. 4,166,182, incorporated herein in its entirety by reference, describes the preparation of pergolide and its oral or parenteral administration as a prolactin inhibitor and in the treatment of Parkinson's Disease.

German patent application DE 4240798, incorporated herein its entirety by reference, describes a pharmaceutical composition containing ergot derivatives, including pergolide, for protection of nerves. The composition may be delivered orally, sublingually, parenterally, percutaneously or nasally.

U.S. Pat. No. 4,797,405 incorporated herein in its entirety by reference, discusses stabilized pergolide oral compositions that demonstrate reduced decomposition when exposed to light.

The dopaminergic agonist effect of pergolide has resulted in its use in a variety of treatments, in addition to the treatment of Parkinson's Disease. For example, U.S. Pat. No. 4,800,204, incorporated herein in its entirety by reference, discusses a method of controlling tobacco use by orally or parenterally administering a direct dopamine receptor agonist such as pergolide.

U.S. Pat. No. 4,935,429, incorporated herein in its entirety by reference, discusses a method of treating psychostimulant abuse by orally or parenterally administering a dopamine agonist such as pergolide.

U.S. Pat. No. 5,063,234, incorporated herein in its entirety by reference, discusses a method of inhibiting bone demineralization by administering, preferably orally, an ergot derivative, such as pergolide.

The oral administration of pergolide in the treatment of Parkinson's Disease is initiated with 0.05 mg/day dosage for the first 2 days. The dosage is then gradually increased by 0.1 or 0.15 mg/day every third day over the next 12 days of therapy. The dosage may-then be increased by 0.25 mg/day every third day until an optimum therapeutic dosage is achieved at a range of about 1.5 to 8.0 mg/day. Generally, the daily dose is divided into three oral doses. The side effects of oral administration include, but are not limited to nausea, vomiting, dizziness and orthostatic hypotension.

The transdermal route of parenteral delivery of drugs and other biologically active agents ("agents") has been proposed for a wide variety of systemically acting and locally acting agents on either a rate-controlled or non-rate-controlled basis and is described in numerous technical publications such as the following: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,704,282; 4,788,062; 4,816,258; 4,849,226; 4,908,027; 4,943,435; and 5,004,610, the disclosures of which are incorporated in their entirety herein by reference. The transdermal administration of a related compound, lisuride, for treating Parkinson's Disease, is disclosed in U.S. Pat. Nos. 5,252,335 and 5,229,129, the disclosures of which are incorporated in their entirety herein by reference.

When first investigated in depth in the late 1960's, the transdermal route of administration appeared to offer many advantages, particularly with respect to agents that had short half lives and therefore required frequent, repeated dosing or were subject to a high degree of first-pass metabolism by the liver when orally administered. Theoretically, the peaks and valleys in blood concentration resulting of frequent periodic doses of short half-life agents would be eliminated and replaced by substantially constant plasma concentration. This would not only improve patient compliance but also would eliminate the alternating periods of high side-effects and ineffective blood concentrations associated with period dosing. It was also thought that administering the agent through the skin directly into the blood stream would eliminate first-pass metabolism of orally administered agents.

It was initially assumed, theoretically, that any short half-life agent of high potency and skin permeability would be suitable for safe and effective transdermal administration. This assumption, however, has not been proven true.

The failure of the transdermal route to fulfill the initial expectations of its potential as an administrative portal was primarily due to the incredible variety of properties with which nature has endowed the skin to permit it to perform its function as the primary barrier to prevent the ingress of foreign substances into the body. See Transdermal Drug Delivery: Problems and Possibilities, B. M. Knepp, et al, CRC Critical Reviews and Therapeutic Drug Carrier Systems, Vol. 4, Issue 1 (1987).

Thus, the transdermal route of administration, rather than being available to every short half-life agent of high potency and skin permeability, was found to be available only to those few agents that possess the proper combination of a host of characteristics, most of which are unpredictable, required to render the agent suitable for safe and effective transdermal administration.

The most significant of these characteristics are the following:

1. Skin Permeability. The permeability of the skin to the agent must be sufficiently high so that the agent can be administered at a therapeutically effective rate through an area of skin no greater than about 200 cm$^2$ and preferably no greater than 50 cm$^2$. The person-to-person variation in skin permeability at similar sites should also be considered.

2. Skin Binding. The skin beneath the transdermal delivery device has the capability of binding or dissolving a certain amount of agent. The amount of agent so bound must be supplied to the skin before the agent can be delivered into the blood stream at therapeutically effective rates. If large amounts of the agent are bound in the skin, significant delays in the onset of therapeutic effect ("lag time") will be observed together with corresponding delays and termination of effect upon removal of the device. The potential also exists for toxic quantities of potent agents to be contained within the skin beneath the device. Skin binding is not related to skin permeability. Agents that are highly permeable may also be highly bound causing a lag time sufficiently long as to render them unsuitable for their intended use.

3. Irritation. The skin reacts to many topically applied substances, particularly those maintained under occlusion, by blistering or reddening accompanied by unpleasant burning, itching, and stinging sensations. Animal models are used to screen for irritation. Animal models, however, often produce both false positives and false negatives. There is also a wide interpersonal variation in susceptibility to irritation. An agent must be minimally irritating in a large percentage of the potential patient population in order to be suitable for safe and effective transdermal administration.

4. Sensitization. Sensitization is an allergic reaction which is induced when an agent is first applied to the skin and is elicited upon continued exposure which may occur immediately or after a long period of seemingly harmless exposure.

The sensitization may be local, elicited by topical exposure, which manifests itself as contact dermatitis accompanied by blistering, itching, reddening and burning at the site of application. More seriously, the sensitization may be systemic, elicited by topical application but manifesting itself by more general allergic reactions at sites other than the site of application. Most seriously, the systemic sensitization may be elicited by oral or intravenous administration of the drug. If the latter occurs, the patient will be unable to take the drug by any route of administration.

Animal models are used to screen for sensitization. Animal models, however, produce both false positives and false negatives. There is also a wide variation in the allergic reaction between individuals as well as between sexes, races and skin types. It is obvious that a useful transdermal agent must be minimally sensitizing in a large percentage of the potential patient population.

5. Pharmacokinetic Properties. The half-life of an agent is the time after administration that half of the amount administered has been eliminated from the body. Because blood concentrations of continuously administered agents will continue to increase for approximately five half-lives before steady-state constant blood concentrations are achieved, an agent must have a relatively short half-life to be suitable for continuous transdermal administration. The transdermal half-lives of most agents have not been determined. When half-lives of agents determined from intravenous administration are compared with half-lives determined from transdermal administration, the transdermal half-lives are generally longer but there can be wide variation in half-life between individuals based upon factors such as age, sex, health, and body type.

6. Pharmacodynamic Properties. Constant blood levels may not produce the desired therapeutic effects. For example, a therapeutic effect may only be observed at peak blood concentration obtained from bolus dosing but the peak concentration cannot be maintained because of side effects associated therewith. Also, continuous administration of many agents produces tolerance that may require either some agent-free interval or continually increasing and therefore potentially hazardous doses of the agent.

7. Potency. Although a certain degree of potency is required for transdermally administered agent to be effective, it is also possible for an agent to be too potent. As potency increases, lower blood concentrations are required and much smaller quantities are administered. Because of normal inter-individual variations and skin permeability, it may not be possible to precisely control whether a patient is receiving 1 µg/hr or 2 µg/hr, for example. For a highly potent agent, a 1 µg/hr administration may be totally ineffective and a 2 µg/hr rate fatal. Thus, the therapeutic index of an agent, which is the ratio of toxic blood concentration to the therapeutic blood concentration, becomes extremely significant. A highly potent agent may also need to have a relatively high therapeutic index in order to be suitable for transdermal administration.

8. Metabolism. One of the perceived advantages of transdermal administration was that it avoided the "first-pass" metabolism of the agent by the liver that is associated with oral administration. It has now been recognized however, that the skin, not the liver, is the largest metabolizing organ in the body. Thus, although first-pass metabolism that occurs after an orally administered agent enters the blood stream can be avoided, skin metabolism, which occurs before the agent enters the bloodstream, cannot be avoided. Skin metabolism is capable of creating metabolites that are inert, toxic, or comparable in biological activity to that of the agent. An agent, to be suitable for transdermal administration, must have the metabolic properties that are consistent with its therapeutic use on continuous administration.

The above summarizes the primary characteristics that affect suitability of an agent for transdermal administration that have been recognized to date. There are undoubtedly others, some of which have not yet been recognized, and, in order for an agent to be suitable for transdermal administration, it must possess the right combination of all these characteristics, a combination of which, as illustrated by the very few drugs that are now suitable for administration from transdermal delivery devices, is quite rare and unpredictable.

SUMMARY OF THE INVENTION

It is unexpected that pergolide would be delivered through the skin at meaningful therapeutic rates either as a base or salt because, as its chemical name 8-[(methylthiolmethyl]6-propylergoline monomethanesulfonate)] indicates, it has a complex chemical structure which does not lend itself to readily permeate through biological membranes such as the skin.

Nonetheless, according to this invention, it has been discovered that pergolide can be safely and efficaciously administered transdermally to provide, among other things, treatment for Parkinson's Disease, with a reduced incidence of side effects and improved patient compliance. In addition, the present invention provides methods for the transdermal delivery of pergolide and delivery systems for effecting the same, which are suitable for the administration of pergolide continuously through a body surface or membrane to achieve and maintain therapeutic blood plasma levels of pergolide in a patient. A particularly advantageous aspect of this invention is the ability to maintain substantially constant blood plasma levels of pergolide in a patient over extended periods of time.

As used herein, the term "transdermal" intends both percutaneous and transmucosal administration, ie, passage of pergolide through intact unbroken skin or mucosal tissue into the systemic circulation.

As used herein, the term "pergolide" intends not only the basic form of pergolide but also a pharmaceutically acceptable salt form of pergolide.

As used herein the term "salt" intends, but is not limited to, pharmaceutically acceptable salts such as chlorides, acetates, sulfates, phosphates, mesylates.

As used herein, the term "pergolide therapy" intends all medical conditions for which pergolide is or will be indicated, including, without limitation, as a psychic energizer and in the treatment of Parkinson's Disease, migraine, allergic responses, urticaria, hypertension, endometritis, and other conditions associated with dopaminergic agonists.

As used herein, the term "individual" intends a living mammal and includes, without limitation, humans and other primates, livestock and sports animals such as cattle, pigs and horses, and pets such as cats and dogs.

As used herein, the term "therapeutic effective amount" intends the dose of pergolide that provides pergolide therapy, in the case of adult humans, the optimum dosage range is normally about 1.5 to 8 mg of pergolide per day.

As used herein, the phrase "sustained time period" or "administration period" intends at least about 8 hours and will typically intend a period in the range of about one to about seven days.

As used herein, the phrase "predetermined area of skin" intends a defined area of intact unbroken skin or mucosal tissue. That area will usually be in the range of about 5 cm$^2$ to about 100 cm$^2$.

As used herein, the term "permeation enhancement" intends an increase in the permeability of skin to pergolide in the presence of a permeation enhancer as compared to permeability of skin to pergolide in the absence of a permeation enhancer.

The present invention relates to improved compositions, devices and methods for the transdermal administration of pergolide in the treatment of Parkinson's Disease, among other things. According to the present invention, it has been found that pergolide may be safely and efficaciously administered transdermally through a body surface or membrane at a therapeutically effective rate for a predetermined, sustained time period in order to provide an effective therapeutic result. Another aspect of the present invention is directed to the transdermal administration of pergolide together with a suitable permeation enhancer or mixture of enhancers. Therapeutic blood plasma levels of pergolide in a patient of about 100–2000 pg/ml may be achieved and maintained by the practice of this invention.

The system of the invention comprises a carrier or matrix adapted to be placed in pergolide or pergolide- and permeation-enhancing mixture-transmitting relation to the selected skin or other body site. The carrier or matrix contains sufficient amounts of pergolide or any acceptable pharmaceutical salt thereof to continuously administer to the site, over a predetermined delivery period, pergolide, at a therapeutically effective rate. In another embodiment, the carrier or matrix contains sufficient amounts of pergolide or any acceptable pharmaceutical salt thereof and the permeation-enhancing mixture to continuously coadminister to the site, over a predetermined delivery period, pergolide, at a therapeutically effective rate, and a permeation enhancer or permeation enhancer mixture.

The accompanying figures, which are incorporated in and constitute a part of this specification, illustrate embodiments of the invention and, together with the description serve to explain.the principles of the invention.

DETAILED DESCRIPTION OF THE INVENTION

Figure 1:
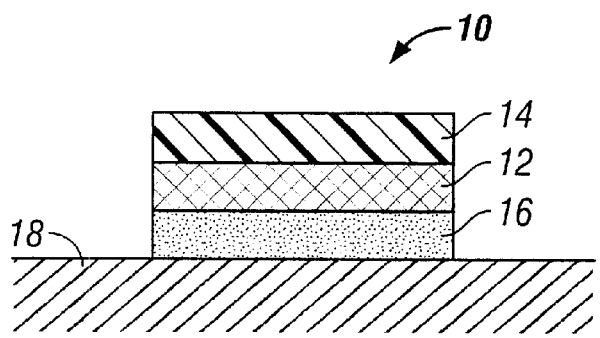
FIG. 1 is a cross-section through a schematic perspective view of one embodiment of a transdermal therapeutic system according to this invention prior to application to the skin.

According to the present invention, it has been found that pergolide may be administered to the human body at a therapeutically effective rate via the transdermal route for the purpose of treating Parkinson's Disease, among other things, when administered alone or coadministered with a suitable permeation enhancer or enhancer mixture. The plasma terminal half-life of pergolide administered transdermally is in the range of 5 to 10 hours, and therapeutic blood plasma levels of 100 pg/ml to 2000 pg/ml can be achieved from administration rates in the range of 30 $\mu$g/hr to 150 $\mu$g/hr. Representative in vitro skin fluxes of pergolide through human skin are in the. range of 0.1 $\mu$g/cm$^2$·hr to 8.0 $\mu$g/cm$^2$·hr, depending on the form of pergolide (base or salt) and the permeation enhancer or enhancer mixture.

Therapeutic blood plasma levels can be achieved within approximately 5 to 10 hours following application of the first patch, and steady state blood plasma concentrations are preferably maintained at about 300–1200 pg/ml with subsequent system applications. When a subsequent system is applied, a lag period of no pergolide delivery is not experienced due to the presence of a skin depot of pergolide remaining from the prior system, thus pergolide is continuously administered throughout subsequent system applications in order to maintain therapeutic blood plasma levels of pergolide over a sustained time period. The range of desired and achievable cumulative release of pergolide, arriving through the skin at a limited area, is 1.5–8.0 mg per 24 hours. The system is easily adapted to provide a cumulative release of pergolide over a 24 hour period of less than 1.5 mg if necessary. Additionally, the system is easily adapted for shorter or longer duration treatments, but generally 72 hours is the preferred duration for a single treatment.

Because the average baseline skin flux of a 2% by weight pergolide. base/water formulation is about 0.3 $\mu$g/cm$^2$·hr over a period of 50 hours, a permeation increase of greater than 10× is required in order to administer the minimum preferred therapeutic daily dosage of 1.5 mg of pergolide from a 20 cm$^2$ system. A 2% by weight pergolide6mesylate/water formulation has an average baseline skin flux of about 1.1 $\mu$g/cm$^2$·hr over a 50 hour period, thus requiring a permeation increase of at least 3× in order to achieve this minimum desired dosage from a 20 cm$^2$ system. Accordingly, there is a need to increase the pergolide skin flux.

The desired pergolide admininstration rate may be achieved by increasing the surface area of the transdermal delivery device without increasing the flux. For example, for a pergolide skin flux of 1.1 $\mu$g/cm$^2$·hr, the surface area of a patch would have to be increased to about 60 cm$^2$ in order to deliver approximately 1.6 mg of pergolide over a 24 hour period.

The flux of pergolide through skin may also be increased by the use of permeation enhancers which include, but are not limited to: monoglycerides such as glycerol monolaurate, glycerol monooleate or glycerol monolinoleate, lactate esters such as lauryl lactate, caproyl lactic acid, lauramide diethanolamine (LDEA), mineral oil, dimethyl lauramide, polyethylene glycol-4 lauryl ether (Laureth-4), and ethanol, alone or in combinations of one or more. An embodiment of this invention also relates to codelivery of at least one of the permeation enhancers mentioned above to aid in the transdermal delivery of pergolide.

The present inventors also found that certain adhesives were preferred as the in-line contact adhesive when one was used in a therapeutic transdermal pergolide system. More particularly, it was found that systems using polyisobutylene adhesives as the in-line contact adhesive resulted in greater flux of pergolide through skin than when other adhesives, such as acrylate adhesives, were used.

Therefore, the present invention, in one embodiment, is directed to a composition of matter for administration to a body surface or membrane to deliver pergolide by permeation through the body surface or membrane at a therapeutically effective rate, wherein the composition comprises an amount of pergolide in a carrier effective to permit sustained release of pergolide at a therapeutically effective rate over an administration period of at least about 8 hours, wherein said therapeutically effective rate of pergolide release achieves therapeutic blood plasma levels of pergolide in a patient over a substantial portion of said administration period.

Another embodiment is directed to a composition of matter for administration to a body surface or membrane to deliver pergolide by permeation through the body surface or membrane at a therapeutically effective rate, wherein the composition comprises, in combination:

(a) a therapeutically effective amount of pergolide or a pharmaceutically acceptable salt form; and (b) a permeation-enhancing amount of a permeation enhancer or mixture of permeation enhancers. The drug may be present in the composition in an amount ranging from 0.1 to 20% by weight.

This invention finds particular usefulness in administering pergolide across skin. It is also useful, however, in administering pergolide across mucosa. According to our invention, pergolide, or pergolide and permeation enhancer or enhancer mixture are placed in drug or drug and permeation-enhancing mixture-transmitting relationship to an appropriate body surface, preferably in a pharmaceutically acceptable carrier thereof, and maintained in place for the desired period of time.

The pergolide and the permeation enhancer or mixture, if used, are typically dispersed within a physiologically compatible matrix or carrier, as more fully described below, which may be applied directly to the body as an ointment, gel, cream, suppository or sublingual or buccal tablet. When used in the form of a liquid, ointment, lotion, cream or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of topical compositions as are known to the art.

In other embodiments, the pergolide or pergolide and permeation enhancer or mixture would be administered from a transdermal device as more fully described below. Examples of suitable transdermal delivery devices are illustrated in FIGS. 1, 2, 3 and 4. In the figures, the same reference numbers are used throughout the different figures to designate the same or similar components. The figures are not drawn to scale.

Referring now to FIG. 1, a preferred embodiment of a transdermal therapeutic system according to this invention comprises transdermal delivery device 10 comprising a reservoir 12 containing pergolide or a pharmaceutically acceptable salt. Reservoir 12 would also contain the permeation-enhancing compound or mixture, if used. Reservoir 12 is preferably in the form of a matrix containing pergolide or pergolide and the permeation enhancer or enhancer mixture dispersed therein. Reservoir 12 is sandwiched between a backing 14 and an in-line contact adhesive layer 16. The device 10 adheres to the surface of the skin 18 by means of the adhesive layer 16. The adhesive layer 16 may optionally contain the permeation-enhancing compound and/or pergolide. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16. Although the preferred embodiments of this invention utilize an in-line adhesive as is shown in FIG. 1, other means for maintaining the system on the skin can be employed. Such means include a peripheral ring of adhesive outside the path of the drug from the system to the skin or the use of other fastening means such as buckles, belts, and elastic arm bands.

Figure 2:
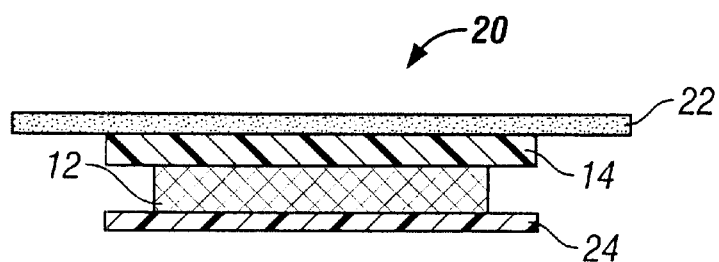
FIG. 2 is a cross-section view through another embodiment of this invention.

Alternatively, as shown in FIG. 2, transdermal therapeutic device 20 may be attached to the skin or mucosa of a patient by means of an adhesive overlay 22. Device 20 is comprised of reservoir 12 containing pergolide or a pharmaceutically acceptable salt and a permeation-enhancing compound or mixture, if used. Reservoir 12 is preferably in the form of a matrix containing the pergolide or pergolide and permeation enhancing compound dispersed therein. A backing layer 14 is provided adjacent one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

Figure 3:
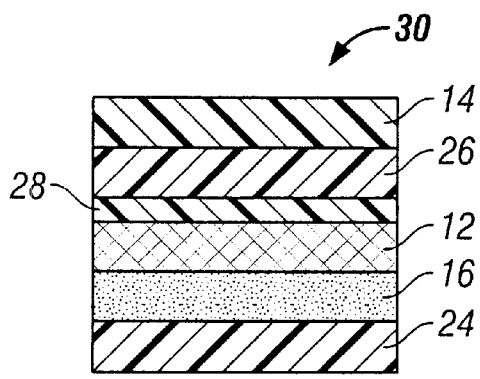
FIG. 3 is a cross-section view through another embodiment of this invention.

In FIG. 3, transdermal delivery device 30 comprises a pergolide and permeation-enhancing compound-containing reservoir ("pergolide reservoir") 12 substantially as described with respect to FIG. 1. Permeation enhancer reservoir ("enhancer reservoir") 26 comprises the permeation-enhancing compound or mixture dispersed throughout and contains pergolide at or below saturation, when in equilibrium with the first reservoir. Enhancer reservoir 26 is preferably made from substantially the same matrix as is used to form pergolide reservoir 12. A rate-controlling membrane 28 for controlling the release rate of the permeation enhancer from enhancer reservoir 26 to pergolide reservoir 12 is placed between the two reservoirs. A rate-controlling membrane (not shown in FIG. 3) for controlling the release rate of the enhancer from pergolide reservoir 12 to the skin may also optionally be utilized and would be present between adhesive layer 16 and reservoir 12.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate, ethylene n-butyl acetate and ethylene vinyl acetate copolymers.

Superimposed over the permeation enhancer reservoir 26 of device 30 is a backing 14. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S. Pat. No. 4,379,454 (noted above), for example, and as illustrated in FIG. 4. Device 40 shown in FIG. 4 comprises a backing member 14 which serves as a protective cover for the device, imparts structural support, and substantially keeps components in device 40 from escaping the device. Device 40 also includes reservoir 12, which contains the pergolide or pergolide and permeation-enhancer compound, and bears on its surface distant from backing member 14, a rate-controlling membrane 28 for controlling the release of pergolide and/or permeation-enhancing compound from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a strippable liner 24 which would be removed prior to application of the device 40 to the skin.

Figure 4:
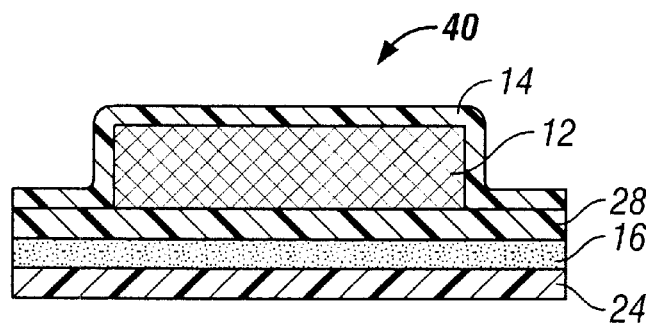
FIG. 4 is a cross-section view through another embodiment of this invention.

In an alternative embodiment of device 40 of FIG. 4, reservoir 12 contains the permeation-enhancing compound and contains pergolide at or below saturation. The pergolide and an additional amount of permeation-enhancing mixture are present in adhesive layer 16, which acts as a separate reservoir.

The pergolide with or without the permeation-enhancing mixture can be administered to human skin or mucosa by direct application to the skin or mucosa in the form of an ointment, gel, cream or lotion, for example, but are preferably administered from a skin patch or other known transdermal delivery device which contains a saturated or unsaturated formulation of the pergolide or pergolide and enhancer. The formulation may be aqueous or non-aqueous based. The formulation should be designed to deliver the pergolide or the pergolide and the permeation-enhancing mixture at the necessary fluxes. Aqueous formulations typically comprise water or water/ethanol and about 1–5 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with the drug and the permeation-enhancing mixture, if used, in addition to any other components in the formulation.

The reservoir matrix should be compatible with pergolide, the permeation enhancer, and any carrier therefor. The term "matrix" as used herein refers to a well-mixed composite of ingredients fixed into shape. When using an aqueous-based formulation, the reservoir matrix is preferably a hydrophilic polymer, eg, a hydrogel.

When using a non-aqueous based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would consist essentially of a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA. Polyisobutylene/oil polymers containing from 4–25% high molecular weight polyisobutylene and 20–81% low molecular weight polyisobutylene with the balance being an oil such as mineral oil or polyisobutynes may also be used as the matrix material.

The amount of pergolide present in the therapeutic device and required to achieve an effective therapeutic result depends on many factors, such as the minimum necessary dosage of the pergolide for the particular indication being treated; the solubility and permeability of the matrix, taking into account the presence of a permeation enhancer, of the adhesive layer and of the rate-controlling membrane, if present; and the period of time for which the device will be fixed to the skin. The minimum amount of pergolide is determined by the requirement that sufficient quantities of pergolide must be present in the device to maintain the desired rate of release over the given period of application. The maximum amount for safety purposes is determined by the requirement that the quantity of pergolide present cannot exceed a rate of release that reaches toxic levels.

The pergolide is normally present in the matrix or carrier at a concentration in excess of saturation, the amount of excess being a function of the desired length of the delivery period of the system. Pergolide may, however, be present at a level below saturation without departing from this invention as long as it is continuously administered to the skin or mucosal site at a therapeutic rate and for a period of time sufficient to deliver a therapeutically effective amount of pergolide that provides the desired therapeutic result.

The permeation enhancer useful in the present invention is selected from those compounds which are compatible with pergolide or its pharmaceutically acceptable salt and which provide enhanced skin permeation to the drug when it is administered together with the drug to the skin of a user. Additionally, the permeation enhancer must not adversely interact with the adhesive of the in-line contact adhesive layer if one is present. Such permeation enhancers can be selected from, but are not limited to, $C_{2-4}$ alcohols such as ethanol and isopropanol, polyethylene glycol monolaurate, laureth-4, lauryl lactate, dimethyl lauramide, LDEA, caproyl lactic acid, mineral oil, esters of fatty acids having from about 10 to about 20 carbon atoms, and monoglycerides or mixtures of monoglycerides of fatty acids alone, or in combinations with each other.

Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% and a total monoesters content of 58%. Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid.

Monoglyceride permeation enhancers include glycerol monooleate, glycerol monolaurate and glycerol monolinoleate, for example. In a presently preferred embodiment of this invention, the permeation enhancer is a monoglyceride or a mixture of monoglycerides of unsaturated fatty acids, and more preferred is glycerol monolaurate (GML) with lauryl lactate or laureth-4. As used herein and in the appended claims, the term "monoglyceride" refers to a monoglyceride or a mixture of monoglycerides of fatty acids.

It has been seen that glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the permeation enhancer, the glycerol monooleate must have a total monoesters content of at least 65%.

The permeation-enhancing mixture is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

In addition to the pergolide and permeation-enhancing mixture, the matrix or carrier may also contain dyes, pigments, inert fillers, excipients and other conventional components of pharmaceutical products or transdermal devices known to the art.

Because of the wide variation in skin permeability from individual to individual and from site to site on the same body, it may be preferable that the pergolide, or pergolide and permeation-enhancing compound, be administered from a rate-controlled transdermal delivery device. Rate control can be obtained either through a rate-controlling membrane or adhesive or both as well as through the other means.

A certain amount of pergolide will bind reversibly to the skin, and it is accordingly preferred that the skin-contacting layer of the device include this amount of pergolide as a loading dose.

The surface area of the device of this invention can vary from about 1–200 $cm^2$. A typical device, however, will have a surface area within the range of about 5–50 $cm^2$, preferably about 20 $cm^2$.

The devices of this invention can be designed to effectively deliver pergolide for an extended time period of from several hours up to 7 days or longer. Seven days is generally the maximum time limit for application of a single device because the adverse affect of occlusion of a skin site increases with time and the normal cycle of sloughing and replacement of the skin cells occurs in about 7 days.

Preferably, the transdermal drug delivery device contains sufficient amounts of permeation-enhancing compound as described above and of pergolide, in combination, to provide systemic administration of pergolide through the skin at a therapeutically effective rate and for a predetermined period of time for the pergolide to provide an effective therapeutic result.

Preferably, a device for the transdermal administration of pergolide, at a therapeutically effective rate, comprises:
  (a) a reservoir comprising:
    (i) 1–15% by weight pergolide,
    (ii) 10–50% by weight of a permeation enhancer or permeation enhancing mixture, (iii) 35 to 85% by weight ethylene vinyl acetate having a vinyl acetate content of 9–60%;

(b) a backing on the skin-distal surface of the reservoir; and (c) means for maintaining the reservoir in drug- and permeation-enhancing mixture-transmitting relation with the skin.

More preferably, a device for the transdermal administration of pergolide, at a therapeutically effective rate, comprises:

(a) a reservoir comprising:
  (i) 5 to 15% by weight pergolide,
  (ii) 10 to 30% by weight of permeation enhancer or permeation enhancing mixture,
  (iii) 45 to 85% by weight ethylene vinyl acetate having a vinyl acetate content of 9–40%;

(b) a backing on the skin-distal surface of the reservoir; and (c) means for maintaining the reservoir in drug- and permeation-enhancing mixture-transmitting relation with the skin.

Most preferably, a device for the transdermal administration of pergolide, at a therapeutically effective rate, comprises:

(a) a reservoir comprising:
  (i) 10 to 15% by weight pergolide,
  (ii) 10 to 30% by weight of a permeation enhancer or permeation enhancing mixture,
  (iii) 45 to 80% by weight ethylene vinyl acetate having a vinyl acetate content of 30–40%;

(b) a backing on the skin-distal surface of the reservoir; and (c) means for maintaining the reservoir in drug- and permeation-enhancing mixture-transmitting relation with the skin.

The backing may be a breathable or occlusive material such as polyethylene, polyurethane, polyester or ethylene vinyl acetate films. An occlusive Medpar® backing is preferred. If an ethylene vinyl acetate is employed as the backing, preferably, it has an acetate content of 33% or 40%.

The means for maintaining the reservoir in drug and permeation-enhancing mixture transmitting relation with the skin are preferably a polyisobutylene adhesive, as described in the Examples that follow. A further embodiment of the invention is directed to including in the adhesive a small percentage, eg, from about 2.5 to about 5 wt % of the pergolide or pharmaceutically acceptable salt.

The aforementioned patents describe a wide variety of materials which can be used for fabricating various layers or components of the transdermal pergolide delivery systems according to this invention. This invention, therefore, contemplates the use of other materials other than those specifically disclosed herein including those which may become hereafter known to the artist capable of forming the necessary functions.

The invention is also directed to a method of continuously administering pergolide to a patient at a therapeutically effective rate over an administration period in order to provide substantially constant therapeutically effective blood plasma levels of pergolide in a patient throughout a substantial portion of said administration period. Therapeutic blood plasma levels of pergolide in a patient may be preferably maintained at about 100–2000 pg/ml, more preferably at about 300–1200 pg/ml.

Another method of the present invention is directed to a method for the transdermal coadministration of pergolide at a therapeutically effective rate together with a skin permeation-enhancing amount of a permeation enhancer or enhancer mixture in order to achieve and maintain therapeutic blood levels of pergolide in a patient, comprising:

(a) coadministering to a body surface or membrane, pergolide; and (b) a permeation-enhancing compound or mixture, wherein pergolide is delivered at a therapeutically effective rate during a predetermined time period in order to achieve and maintain therapeutic blood levels of pergolide in a patient. The pergolide and permeation-enhancing compound or mixture may be administered to the body surface or membrane by means of the devices and compositions described above.

A preferred embodiment of the present invention comprises a method of treating Parkinson's Disease. To be useful in treating Parkinson's Disease, pergolide should be present in plasma at concentrations above about 100 pg/ml, preferably at concentrations above about 300 pg/ml and most preferably at concentrations of about 1000 pg/ml. To achieve this result, pergolide is delivered at a therapeutic rate of at least about 100 µg per hour, but typically of at least 125 µg/hr, and more typically at about 150 µg/hr, for the treatment period, usually about 12 hours to 7 days. For example, a 20 cm² system would require a pergolide flux through skin of 7.5 µg/cm²·hr in order to achieve the desired therapeutic rate of 150 µg/hr. Such a system would deliver approximately 3.6 mg of pergolide over a 24 hour period.

The length of time of pergolide presence and the total amount of pergolide in the plasma can be changed following the teachings of this invention to provide different treatment regimens. Thus, they can be controlled by the amount of time during which exogenous pergolide is delivered transdermally to an individual or animal.

Having thus generally described our invention, the following specific examples describe preferred embodiments thereof but are not intended to limit the invention in any manner.

EXAMPLE 1

Figure 5:
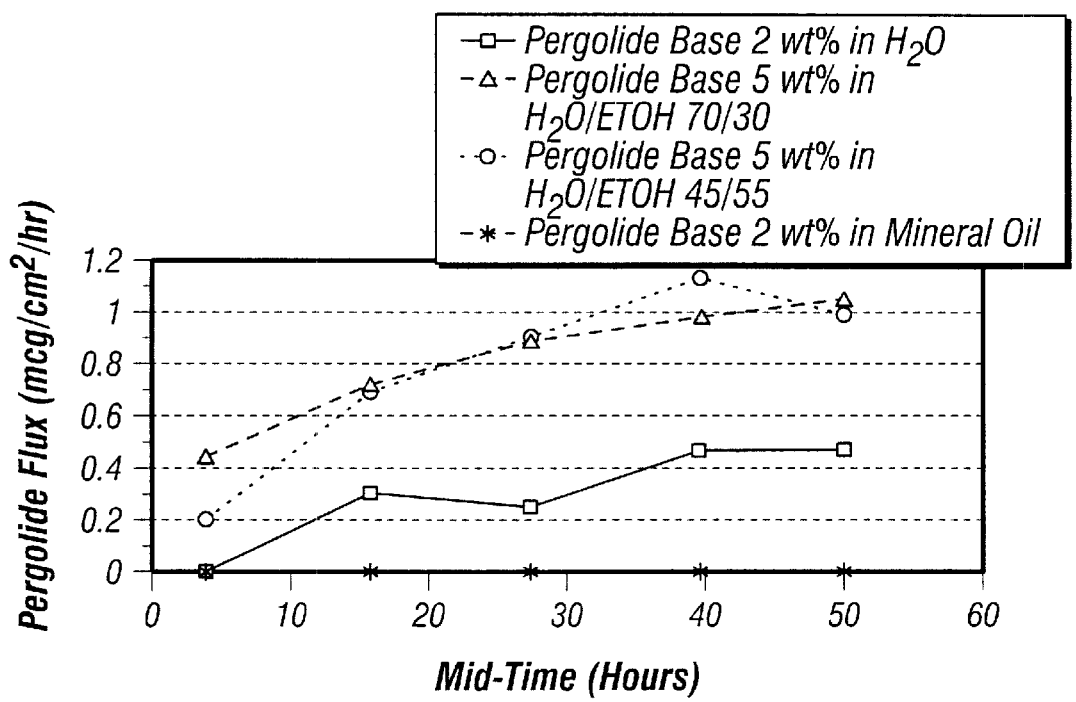
FIG. 5 is a graph of the flux of pergolide base through human epidermis, in vitro, at 35° C., from various aqueous and non-aqueous donors.
Figure 6:
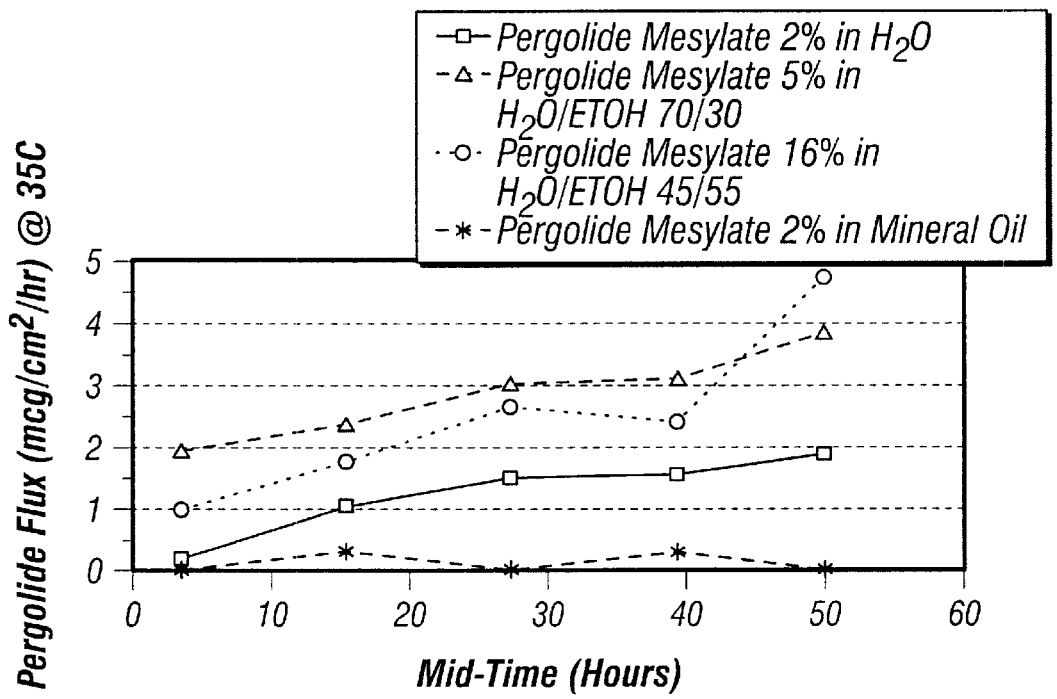
FIG. 6 is a graph of the flux of pergolide mesylate through human epidermis, in vitro, at 35° C., from various aqueous and non-aqueous donors.

Several test samples were made to measure the flux of pergolide base and mesylate through human cadaver epidermis from donor vehicles containing the pergolide base or mesylate mixed with water alone, water and ethanol, or mineral oil alone as shown in Table 1. Transdermal fluxes were obtained using human epidermis at 35° C. in standard diffusion cells. FIGS. 5 and 6 graphically depict the results. As seen in these Figures, the average baseline skin flux of pergolide base without any permeation enhancer is approximately 0.3 µg/cm²·hr over a fifty hour period, while the average baseline skin flux of pergolide mesylate without permeation enhancers is approximately 1.1 µg/cm²·hr over the same time period.

TABLE 1

Aqueous and Non-Aqueous Donor Solutions (weight percent)

| Pergolide | H$_2$O | EtOH | Mineral Oil |
| --- | --- | --- | --- |
| Base 2 | 98 | 0 | 0 |
| Base 5 | 45 | 55 | 0 |
| Base 5 | 70 | 30 | 0 |
| Base 2 | 0 | 0 | 98 |
| Mesylate 2 | 98 | 0 | 0 |
| Mesylate 5 | 45 | 55 | 0 |
| Mesylate 5 | 70 | 30 | 0 |
| Mesylate 2 | 0 | 0 | 98 |

EXAMPLE 2

The drug/permeation enhancer reservoirs were prepared by mixing ethylene vinyl acetate having a vinyl acetate content of 40 percent ("EVA 40", USI Chemicals, Illinois), with pergolide base or mesylate, GML or LDEA, and mineral oil. The mixture was then dissolved in tetrahydrofuran. After blending, the mixture was hand cast and dried to a 5 mil. thick film. The composition of the drug reservoirs is shown in Table 2.

TABLE 2

Drug/Permeation Enhancer Reservoir Composition (weight percent).

| Pergolide | LDEA | Glycerol Monolaurate | Mineral Oil | EVA 40 |
|---|---|---|---|---|
| Base 10 | 15 | 0 | 15 | 60 |
| Base 10 | 0 | 20 | 14 | 56 |
| Mesylate 10 | 15 | 0 | 15 | 60 |
| Mesylate 10 | 0 | 20 | 14 | 56 |

The film was then laminated to a pigmented medium density polyethylene/aluminum foil/PET/EVA (Medpar®) backing on one side and an acrylate contact adhesive on the opposite side (3M). The laminate was then punched down to an area of 1.6 cm².

Circular pieces of human epidermis were placed with stratum corneum facing up. The release liner of the laminate was removed and the system was centered over the stratum corneum side of the epidermis. The edges of epidermis were then folded around the system. This assembly was then mounted on a Teflon rod. A known volume of receptor solution was then placed in a test tube and was equilibrated at 35° C. The Teflon rod with system and epidermis attached was then placed in a water bath at 35° C. Mixing was accomplished by attachment to a motor which caused constant vertical mixing.

Figure 7:
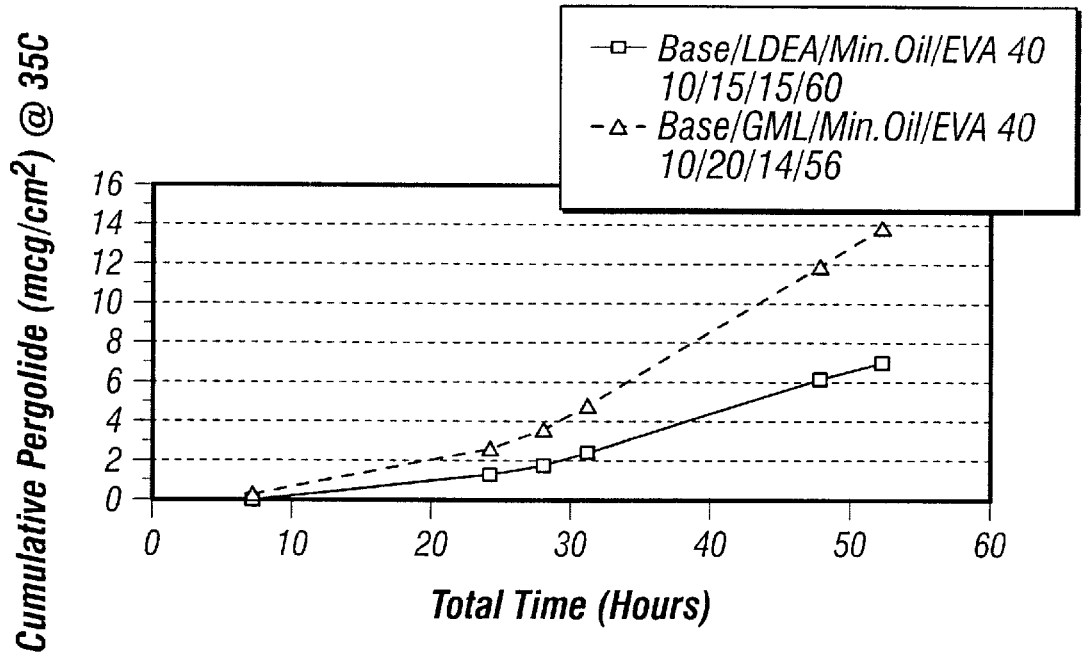
FIG. 7 is a graph of the cumulative release of pergolide base through human epidermis at 35° C., in vitro from an EVA matrix system with various permeation enhancers.
Figure 8:
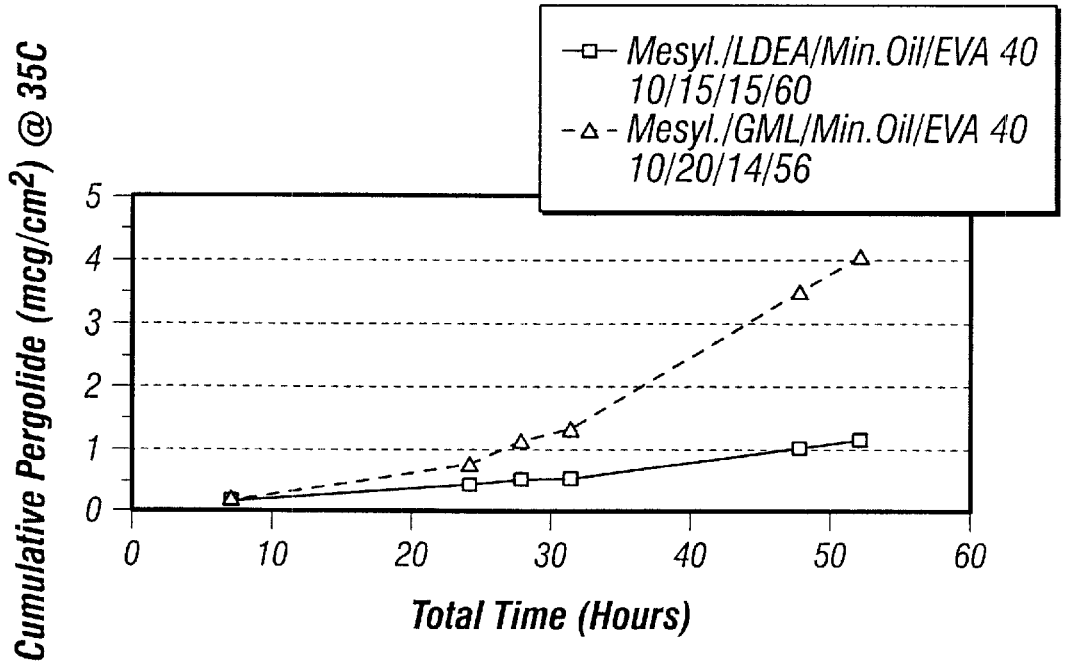
FIG. 8 is a graph of the cumulative release of pergolide mesylate through human epidermis at 35° C., in vitro, from an EVA matrix system with various permeation enhancers.

At given time intervals, the entire receptor solution was removed from the test tubes and replaced with an equal volume of fresh receptor solutions previously equilibrated at 35° C. The receptor solutions are stored in capped vials at room temperature until assayed for pergolide content by HPLC. From the drug concentration and the volume of the receptor solutions, the area of permeation and the time interval, the flux of the drug through the epidermis was calculated as follows: (drug concentration X volume of receptor)/(area x time)=flux ($\mu$g/cm²·hr). The cumulative release of the pergolide base or mesylate is shown in FIGS. 7 and 8.

EXAMPLE 3

The drug/permeation enhancer reservoirs were prepared according to Example 2. The film was then laminated to Medpar backing on one side and a polyisobutylene adhesive containing 2.5% by weight of pergolide on the other. The adhesive was prepared by dissolving 19.8% 1.2M polyisobutylene, 24.7% 35K polyisobutylene and 55.5% light mineral oil in heptane. The 2.5% pergolide was added and the entire mixture was cast to a dry thickness of 2 mils. The film was then cut into circles using a stainless steel punch with an area of 1.6 cm².

The epidermis was separated from the dermis of the skin donor after immersion in 60° C. water for 60 seconds. Discs (⅞-inch diameter) were cut from the epidermis, and the discs were kept at 4° C. in a hydrated state until they were used.

Figure 9:
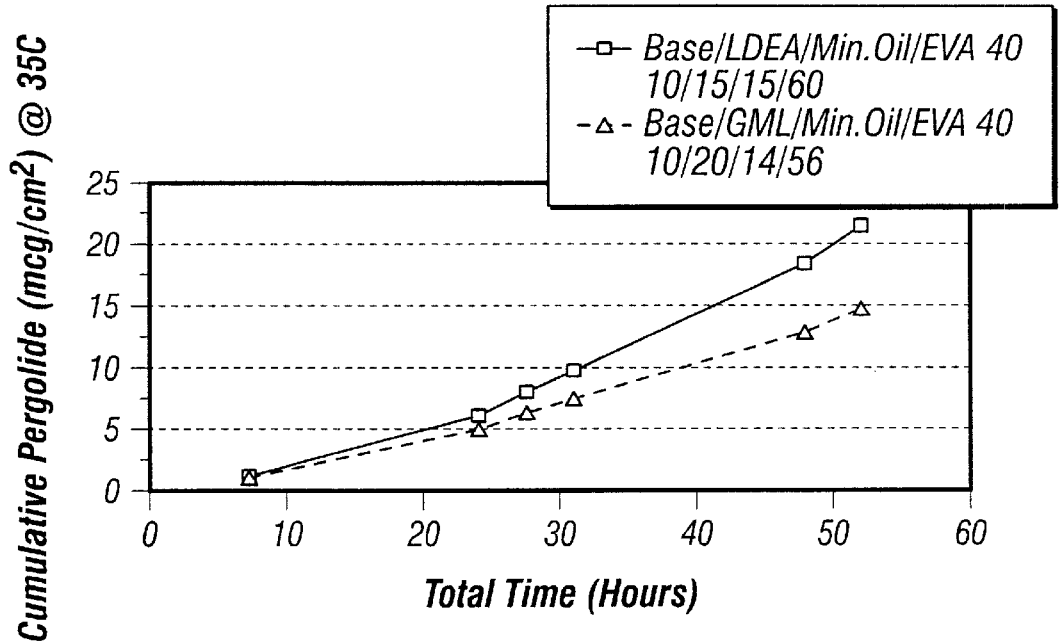
FIG. 9 is a graph of the cumulative release of pergolide base through human epidermis at 35° C. in vitro, from an EVA matrix system with various permeation enhancers.
Figure 10:
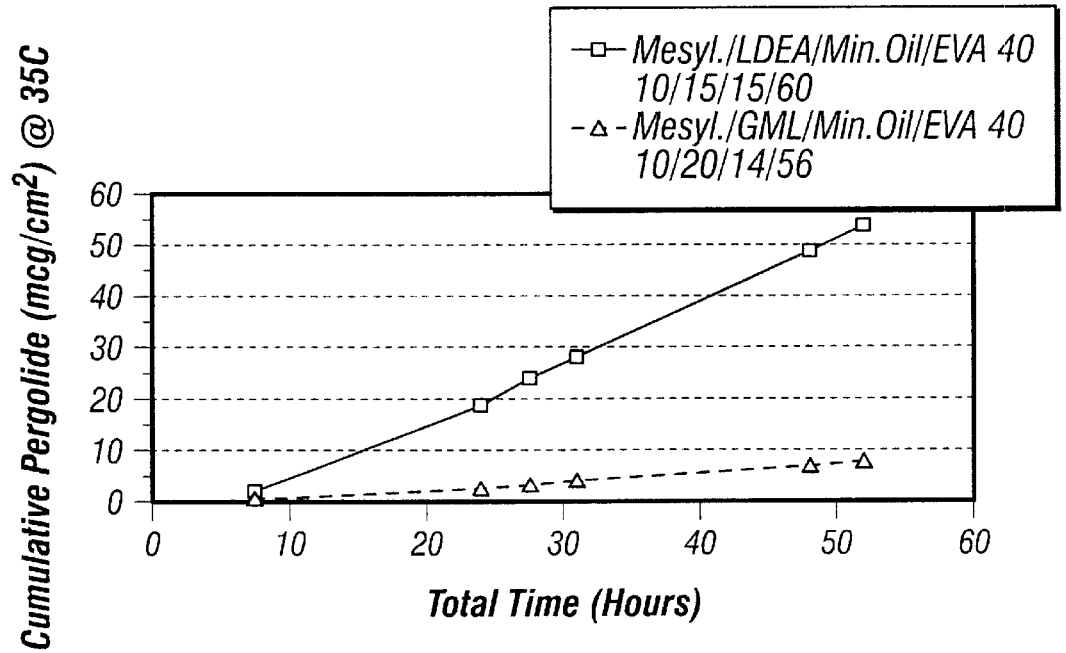
FIG. 10 is a graph of the cumulative release of pergolide mesylate through human epidermis at 35° C., in vitro, from an EVA matrix system with various permeation enhancers.

For each device tested, the release liner was removed and the drug-releasing surface was placed against the stratum corneum side of a disc of epidermis which had been blotted dry just prior to use. The excess epidermis was wrapped around the device so that none of the device edge was exposed to the receptor solution. The device covered with epidermis was attached to the flat side of the Teflon holder of a release rate rod using nylon netting and nickel wire. The rods were reciprocated in a fixed volume of receptor solution. The entire receptor solution was changed at each sampling time. The temperature of the receptor solution in the water bath was maintained at 35° C. The cumulative release of the pergolide base or pergolide mesylate is shown in FIGS. 9 and 10.

EXAMPLE 4

The drug/permeation enhancer reservoirs were prepared by mixing pergolide base or mesylate, EtOH, GML, and caproyl lactic acid (CLA) as shown in Table 3.

TABLE 3

Drug/Permeation Enhancer Reservoir Composition (weight percent)

| Pergolide | EtOH | GML | CLA |
|---|---|---|---|
| Base 10 | 80 | 10 | 0 |
| Base 10 | 90 | 0 | 0 |
| Base 10 | 85 | 0 | 5 |
| Mesylate 10 | 80 | 10 | 0 |
| Mesylate 10 | 90 | 0 | 0 |
| Mesylate 10 | 85 | 0 | 5 |

Figure 11:
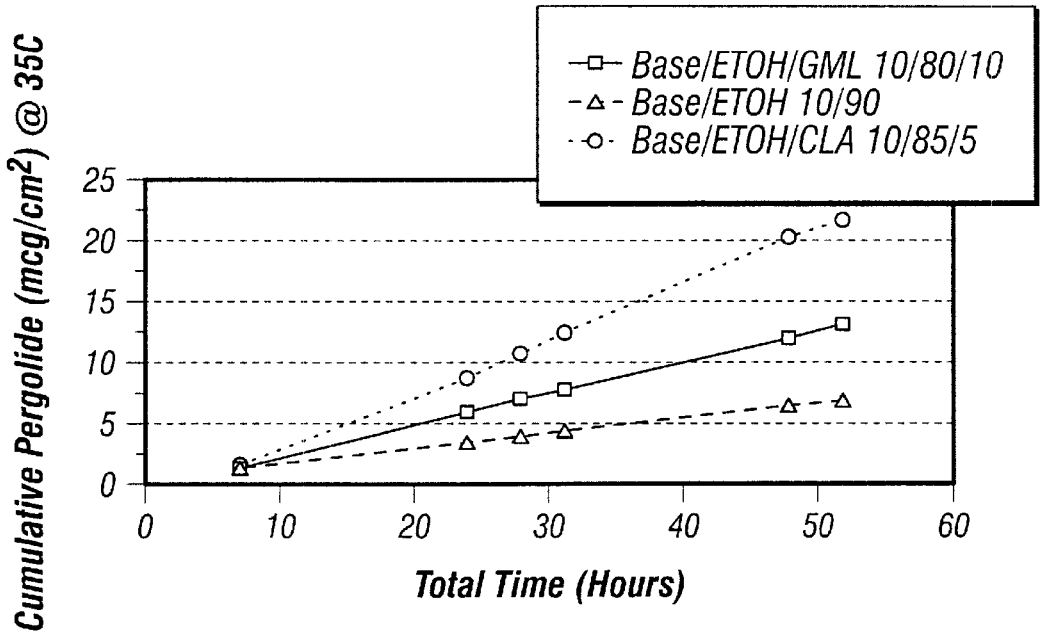
FIG. 11 is a graph of the cumulative release of pergolide base through human epidermis in vitro at 35° C., from an EtOH system having an 18% EVA rate controlling membrane with various permeation enhancers and a polyisobutylene/mineral oil based in-line contact adhesive preloaded with drug.
Figure 12:
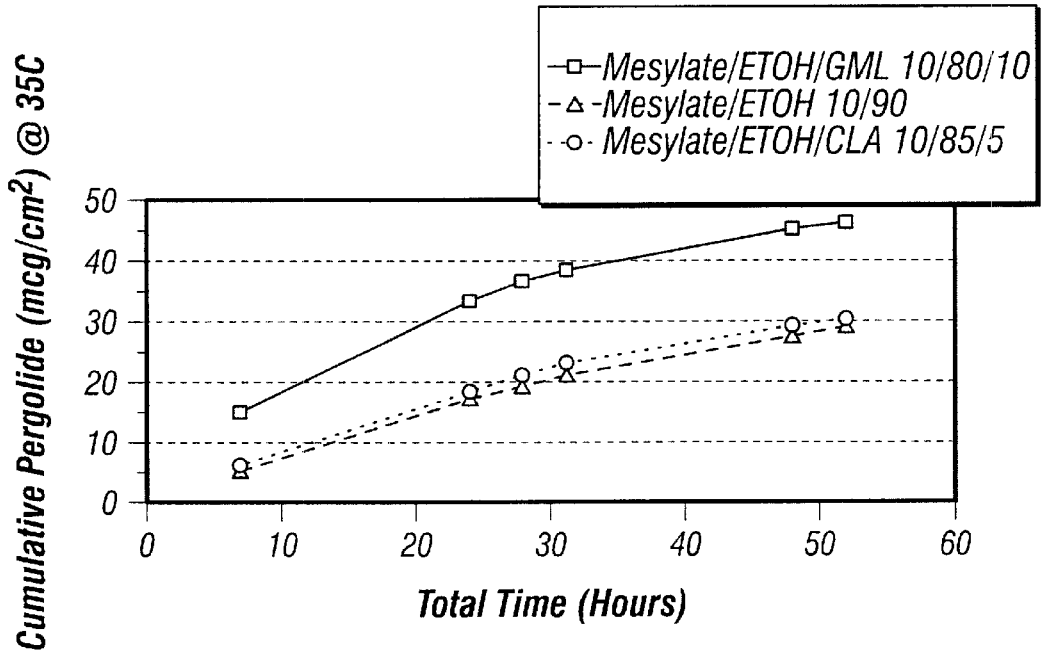
FIG. 12 is a graph of the cumulative release of pergolide mesylate through human epidermis, in vitro, at 35° C., from an EtOH system having an 18% EVA rate controlling membrane with various permeation enhancers and a polyisobutylene/mineral oil based in-line contact adhesive preloaded with drug.

An additional 3% by weight hydroxypropylcellulose and water were added and the mixture was placed in a suitable container and gelled. A desired quantity of the mixture was then applied on the surface of a previously formed trilaminate consisting of a 2 mil thick ethylene vinyl acetate film having a vinyl acetate content of 18% for use as a rate controlling membrane; a polyisobutylene contact adhesive containing 2.5% by weight pergolide; and a polyethylene ethylene terephthalate film coated with silicone for use as a release liner. A Medpar backing was then applied on top of the mixture and the entire system was heat sealed. The systems were then die-cut to the required sizes for use in the in vitro test method described in Examples 2 & 3. The cumulative release of the pergolide base and mesylate are shown in FIGS. 11 and 12.

EXAMPLE 5

Figure 13:
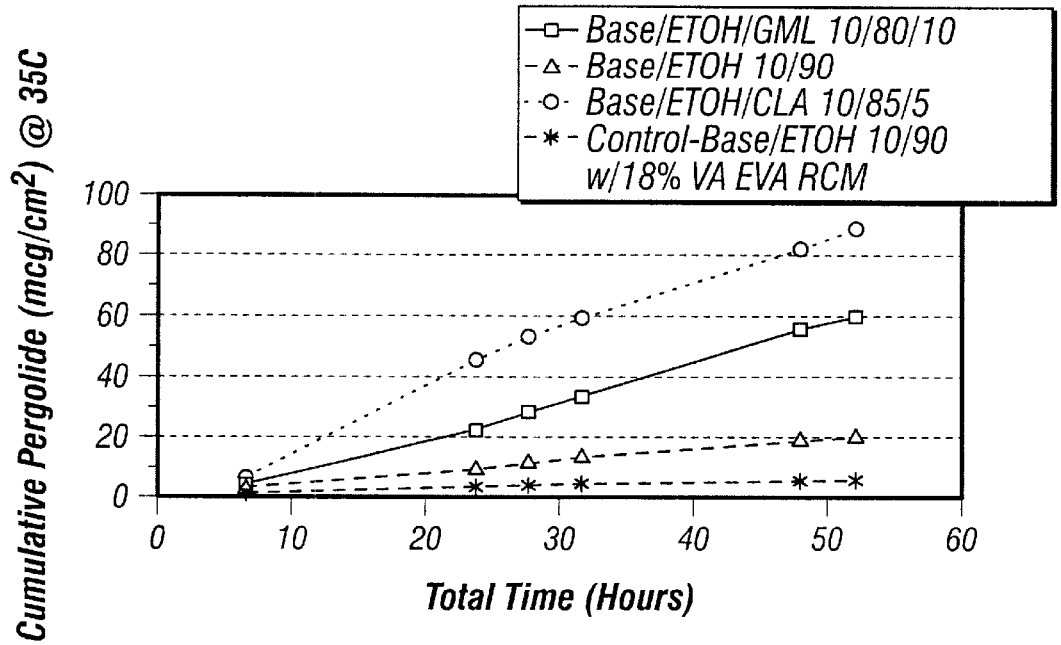
FIG. 13 is a graph of the cumulative release of pergolide base through human epidermis, in vitro, at 35° C., from an EtOH system having a 28% EVA rate controlling membrane with various permeation enhancers.
Figure 14:
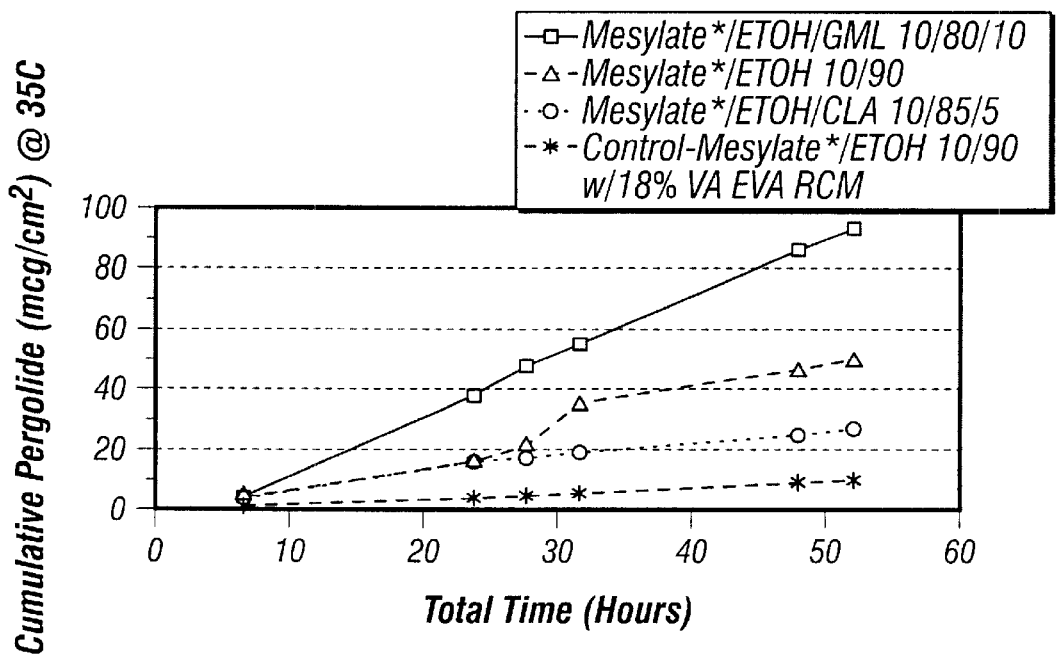
FIG. 14 is a graph of the cumulative release of pergolide mesylate through human epidermis, in vitro, at 35° C., from an EtOH system having a 28% EVA rate controlling membrane with various permeation enhancers.
Figure 15:
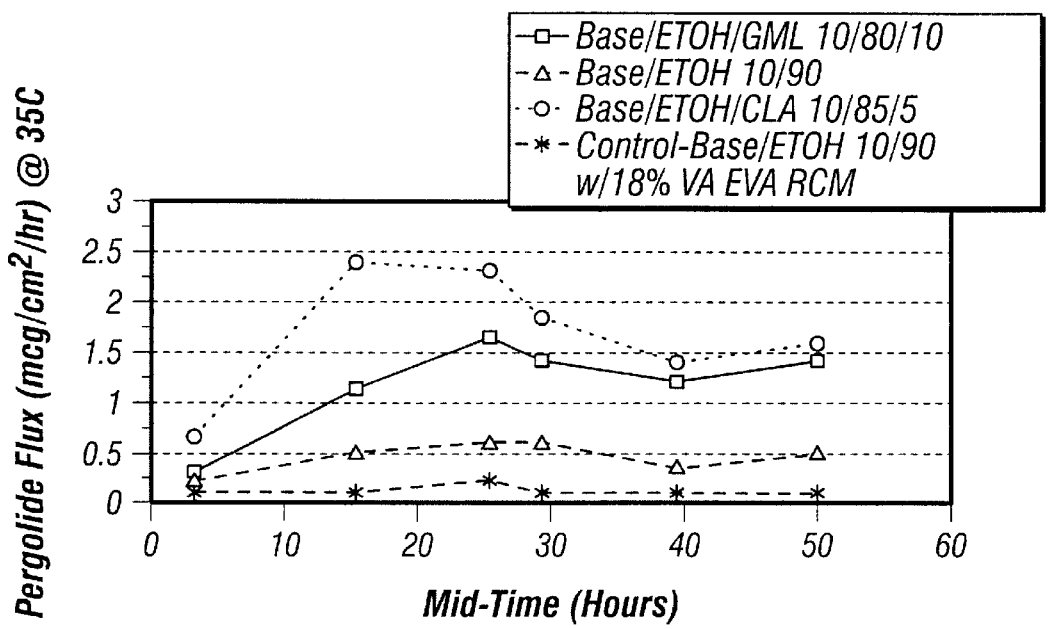
FIG. 15 is a graph of the flux of pergolide base through human epidermis, in vitro, at 35° C., from an EtOH system having a 28% EVA rate controlling membrane with various permeation enhancers and a polyisobutylene/mineral oil based in-line contact adhesive preloaded with drug.
Figure 16:
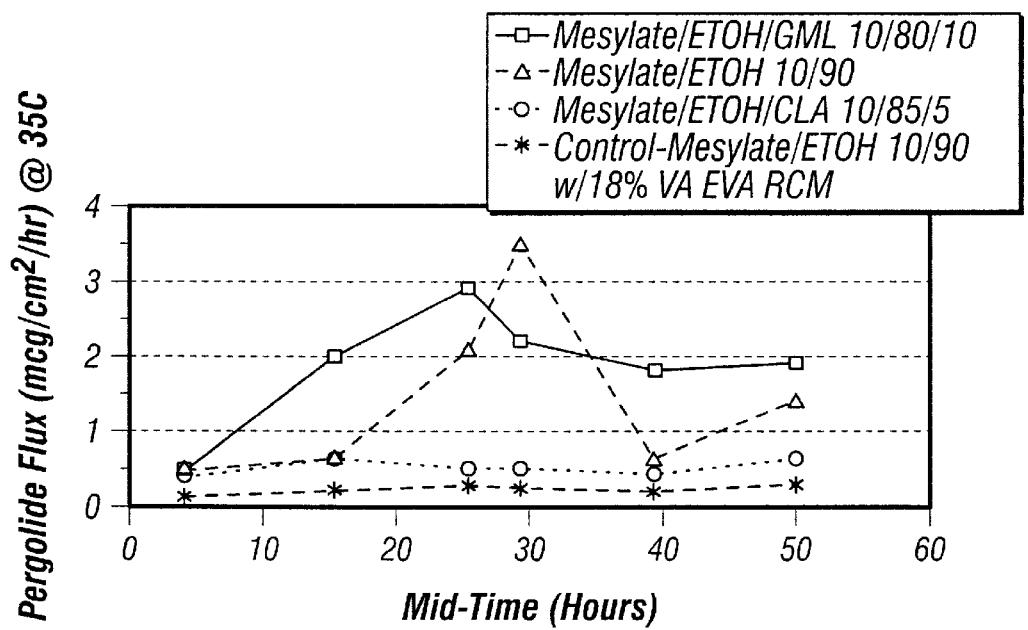
FIG. 16 is a graph of the flux of pergolide mesylate through human epidermis, in vitro, at 35° C., from an EtOH system having a 28% EVA rate controlling membrane with various permeation enhancers and a polyisobutylene/ mineral oil based in-line contact adhesive preloaded with drug.

A desired quantity of the mixture as formed in Example 4 was then applied on the surface of a previously formed trilaminate consisting of a 2 mil thick ethylene vinyl acetate film having a vinyl acetate content of 28% for use as a rate controlling membrane; a polyisobutylene contact adhesive containing 2.5% by weight pergolide; and a polyethylene ethylene terephthalate film coated with fluorocarbon for use as a release liner. A Medpar backing was then applied on top of the mixture and the entire system was heat sealed. The systems were then die-cut to the required sizes for use in the in vitro test method described in Examples 2–4. The cumulative release of the pergolide base and mesylate are shown in FIGS. 13 and 14. The skin flux of the base and mesylate are shown in FIGS. 15 and 16.

EXAMPLE 6

The drug/permeation enhancer reservoirs were prepared by mixing ethylene vinyl acetate having a vinyl acetate content of 40 percent ("EVA 40", USI Chemicals, Illinois), pergolide mesylate, GML, Laureth-4 (L-4), and an optional amount of mineral oil. The mixture was then dissolved in tetrahydrofuran. After blending, the mixture was hand cast and dried to a 5 mil. thick film. The composition of the drug reservoir is shown in Table 4.

TABLE 4

| Drug/Permeation Enhancer Reservoir Composition (weight percent). | | | | |
| --- | --- | --- | --- | --- |
| Pergolide | L-4 | Glycerol Monolaurate | EVA 40 | Mineral Oil |
| Mesylate 10 | 12 | 20 | 48 | 10 |
| Mesylate 10 | 12 | 20 | 48 | 10 |
| Mesylate 10 | 12 | 20 | 58 | 0 |
| Mesylate 10 | 12 | 20 | 58 | 0 |

Figure 17:
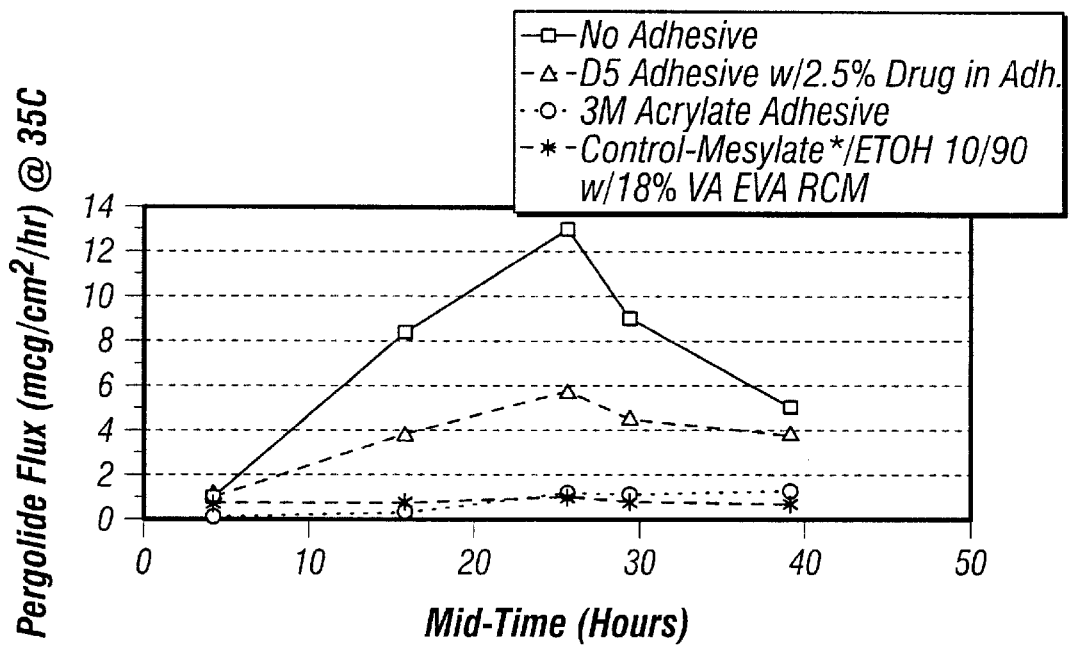
FIG. 17 is a graph of the flux of pergolide mesylate through human epidermis, in vitro, at 35° C., from an Laureth-4/GML/EVA 40 system with and without various in-line adhesives.
Figure 18:
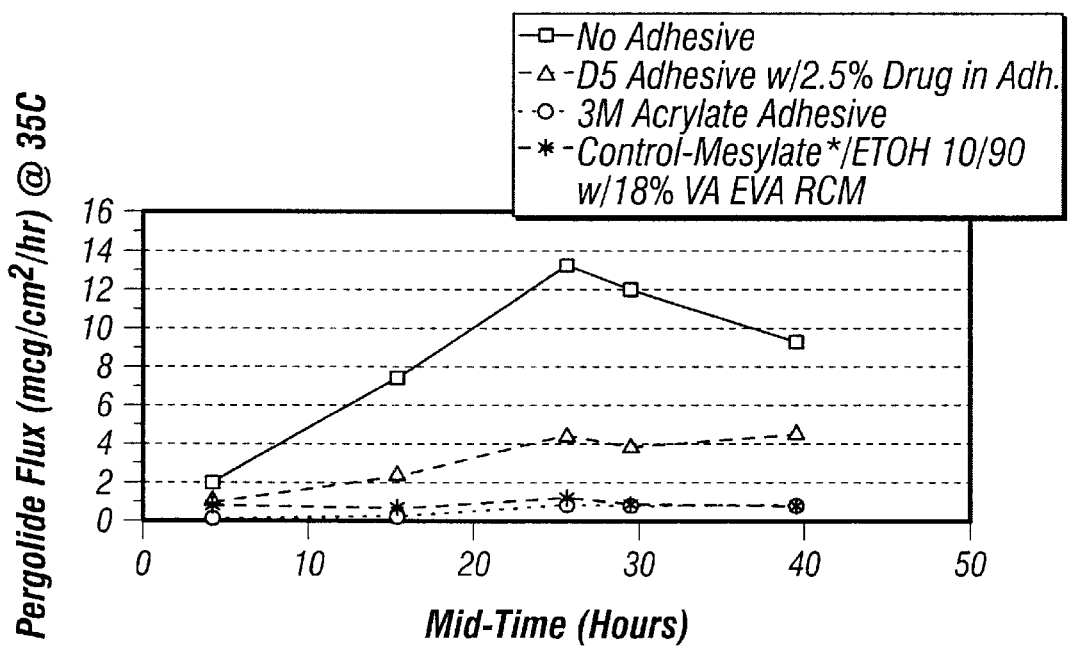
FIG. 18 is a graph of the flux of pergolide mesylate through human epidermis, in vitro, at 35° C., from an Laureth-4/GML/EVA 40/Mineral Oil system with and without various in-line adhesives.
Figure 19:
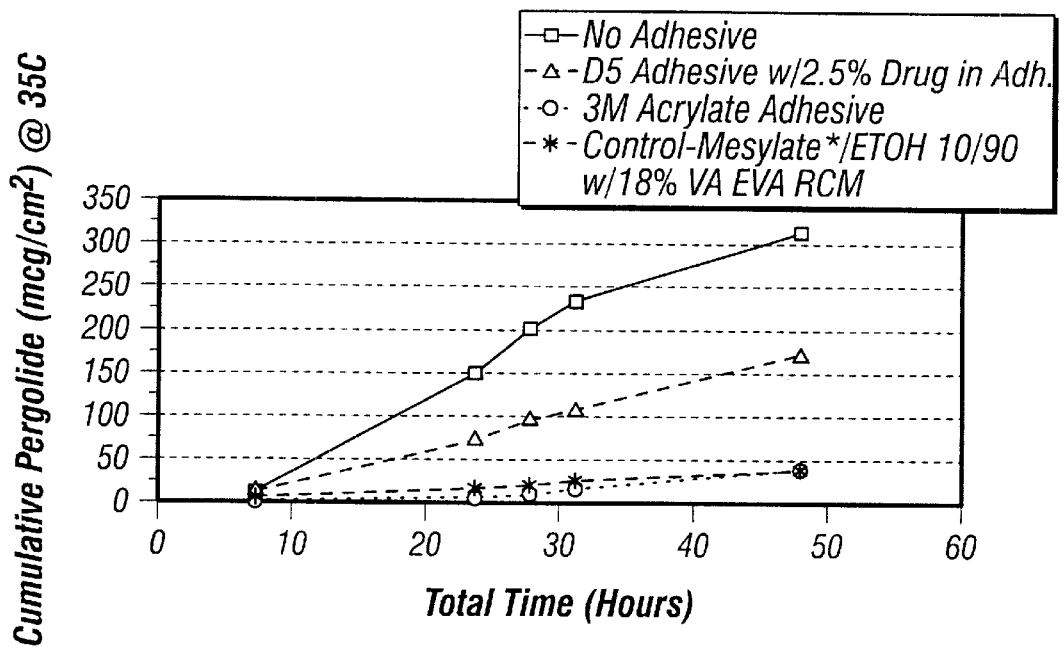
FIG. 19 is a graph of the cumulative release of pergolide mesylate through human epidermis, in vitro, at 35° C., from an Laureth-4/GML/EVA 40/Mineral Oil system with and without various in-line adhesives.
Figure 20:
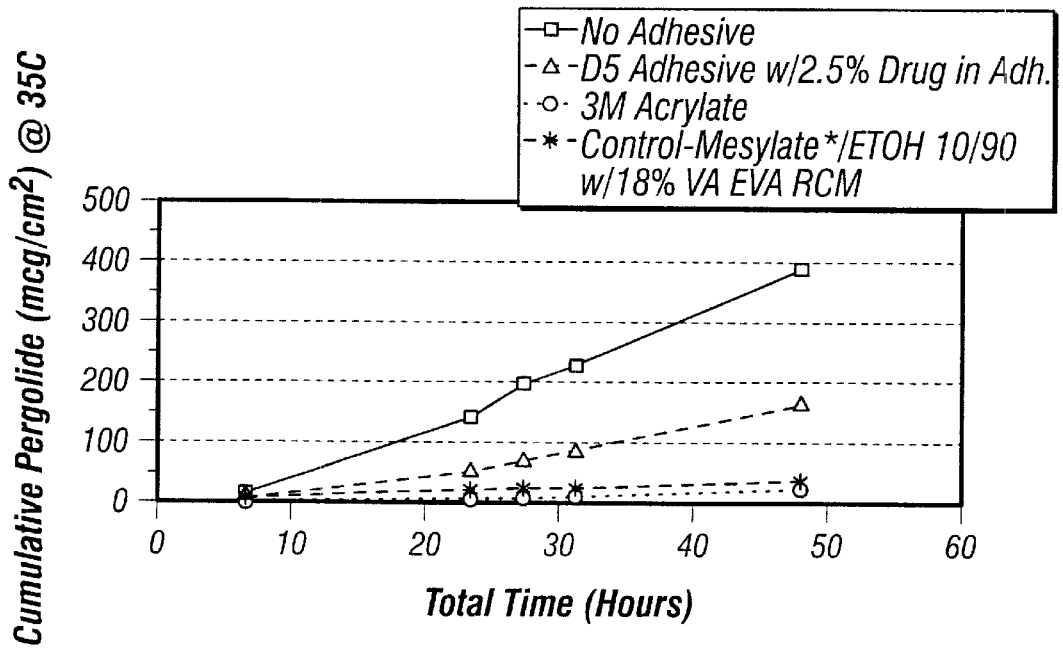
FIG. 20 is a graph of the cumulative release of pergolide mesylate through human epidermis, in vitro, at 35° C., from an Laureth-4/GML/EVA 40 system with and without various in-line adhesives.

The film was then laminated to a Medpar backing on one side. A polyisobutylene adhesive, 3M, or no adhesive was applied on the other side of the film. The systems were then die-cut to the required sizes for use in the in vitro test method described in Examples 2–4. The skin flux of the mesylate is shown in FIGS. 17 and 18. The cumulative release of the mesylate is shown in FIGS. 19 and 20.

Having thus generally described our invention and described certain specific embodiments thereof, including the embodiments that applicants consider the best mode of practicing their invention, it should be readily apparent that various modifications to the invention may be made by workers skilled in the art without departing from the scope of this invention which is limited only by the following claims.

Wherein, what is claimed is:

1. A device for the transdermal administration of a pharmaceutically acceptable salt of pergolide at a therapeutically effective rate, comprising:
    (a) a reservoir comprising an amount of a pharmaceutically acceptable salt of pergolide and being substantially free of pergolide base;
    (b) a backing on or adjacent the body contacting-distal surface of the reservoir; and
    (c) means for maintaining the reservoir in drug transmitting relation with a body surface or membrane wherein the pergolide salt is delivered at a therapeutically effective rate for an administration period of at least 8 hours in order to provide therapeutically effective blood plasma levels of pergolide in a patient over a substantial portion of said administration period.

2. A device according to claim 1 wherein the pergolide salt is present in an amount sufficient to provide said blood plasma levels of at least about 100 pg/mL.

3. A device according to claim 2 wherein the pergolide salt is present in an amount sufficient to provide said blood plasma levels of about 300–1200 pg/mL.

4. A device according to claim 1 wherein the means for maintaining the reservoir in relation with the skin comprises an in-line adhesive layer on the body contacting-proximal surface of the reservoir.

5. A device according to claim 4 wherein the in-line adhesive is a polyisobutylene adhesive.

6. A device according to claim 1 wherein the reservoir further comprises a permeation enhancer or enhancer mixture in an amount sufficient to substantially increase the permeability of the body surface or membrane to the pergolide throughout the administration period.

7. A device according to claim 6 wherein the permeation enhancer is selected from the group consisting of lauramide diethanolamine, monoglycerides or mixtures of monoglycerides of fatty acids, esters of $C_{10}$–$C_{20}$ fatty acids, lactate esters, caproyl lactic acid, ethanol, and polyethylene glycol-4 lauryl ether, alone or in combinations of one or more.

8. A device according to claim 7 wherein the permeation enhancer is a mixture comprising glycerol monolaurate and polyethylene glycol-4 lauryl ether.

9. A device for the transdermal administration of a pharmaceutically acceptable salt of pergolide at a therapeutically effective rate, comprising:
    (a) a first reservoir comprising an amount of a pharmaceutically acceptable salt of pergolide and being substantially free of pergolide base and a permeation-enhancing amount of a permeation enhancer or mixture;
    (b) a second reservoir comprising an excess of the permeation enhancer or mixture and the pharmaceutically acceptable salt of pergolide at or below saturation when in equilibrium with the first reservoir;
    (c) a rate-controlling membrane between the first reservoir and the second reservoir;
    (d) a backing on or adjacent the body contacting-distal surface of the second reservoir; and
    (e) means for maintaining the first and second reservoirs in drug- and permeation enhancing mixture-transmitting relation with a body surface or membrane wherein pergolide is delivered at a therapeutically effective rate for an administration period of at least 8 hours in order to provide therapeutically effective blood plasma levels of pergolide in a patient over a substantial portion of said administration period.

10. A device according to claim 9 wherein the pergolide salt is present in an amount sufficient to provide said blood plasma levels of at least about 100 pg/mL.

11. A device according to claim 10 wherein the pergolide salt is present in an amount sufficient to provide said blood plasma levels of about 300–1200 pg/mL.

12. A device according to claim 9 wherein the permeation enhancer is selected from the group consisting of lauramide diethanolamine, monoglycerides or mixtures of monoglycerides of fatty acids, esters of $C_{10}$–$C_{20}$ fatty acids, lactate esters, caproyl lactic acid, ethanol, and polyethylene glycol-4 lauryl ether, alone or in combinations of one or more.

13. A device according to claim 12 wherein the permeation enhancer is a mixture comprising glycerol monolaurate and polyethylene glycol-4 lauryl ether.

14. A device according to claim 9 wherein the means for maintaining the reservoir in relation with the skin comprises an in-line adhesive layer on the body contacting-proximal surface of the reservoir.

15. A device according to claim 14 wherein the in-line adhesive is a polyisobutylene adhesive.

16. A device for the transdermal administration of a pharmaceutically acceptable salt of pergolide at a therapeutically effective rate, comprising:
    (a) a reservoir comprising:
        (i) 1 to 15 wt % of a pharmaceutically acceptable salt of pergolide and substantially free of pergolide base,
        (ii) 10 to 50 wt % of a permeation enhancer;
        (iii) 35 to 85 wt % of a polymeric carrier;
    (b) a backing on or adjacent the body contacting-distal surface of the reservoir; and
    (c) means for maintaining the reservoir in drug- and permeation enhancing mixture-transmitting relation with a body surface or membrane, wherein pergolide is delivered at a therapeutically effective rate for an administration period of at least 8 hours in order to provide therapeutically effective blood plasma levels of pergolide in a patient over a substantial portion of said administration period.

17. A method for the transdermal administration of a pharmaceutically acceptable salt of pergolide by permeation through a body surface or membrane at a therapeutically effective rate, which method comprises administering a pharmaceutically acceptable salt of pergolide substantially free of pergolide base to a body surface or membrane in a carrier effective to permit sustained release of the pergolide salt through said body surface or membrane over an administration period of at least about 8 hours in order to achieve therapeutically effective blood plasma levels of pergolide in a patient for a substantial portion of said administration period.

18. A method according to claim 17 wherein said blood plasma levels are maintained at about at least 100 pg/mL.

19. A method according to claim 18 wherein said blood plasma levels are maintained at about 300–1200 pg/mL.

20. A method according to claim 17 wherein said pergolide salt is delivered at a rate of at least about 30 μg/hr.

21. A method according to claim 17 further comprising simultaneously coadministering a permeation-enhancing amount of a permeation enhancer compound or mixture which is sufficient to substantially increase the permeability of the body surface or membrane to the pergolide salt throughout the administration period.

22. A method according to claim 21 wherein said blood plasma levels are maintained at about at least 100 pg/mL.

23. A method according to claim 22 wherein said blood plasma levels are maintained at about 300–1200 pg/mL.

24. A method according to claim 21 wherein said pergolide salt is delivered at a rate of at least about 30 μg/hr.

25. A method for treating Parkinson's Disease, the method comprising administering to an area of skin, a pharmaceutically acceptable salt of pergolide substantially free of pergolide base in a carrier effective to permit sustained release of the pergolide salt at a therapeutically effective rate through the skin over an administration period of at least 8 hours in order to provide therapeutically effective blood plasma levels of pergolide in a patient over a substantial portion of said administration period.

26. A device according to claim 9 wherein the pergolide salt is provided in an amount sufficient to deliver about 1.5 to 8 mg of pergolide per day at a flux of at least about 1 μg/cm² hr.

27. A device according to claim 9, 12, or 26 wherein the pharmaceutically acceptable salt is pergolide mesylate.

28. A device according to claim 16 wherein the pergolide salt is provided in an amount sufficient to deliver about 1.5 to 8 mg of pergolide per day at a flux of at least about 1 μg/cm² hr.

29. A device according to claim 28 wherein the permeation enhancer is selected from the group consisting of lauramide diethanolamine, monoglycerides or mixtures of monoglycerides of fatty acids, esters of $C_{10}$–$C_{20}$ fatty acids, lactate esters, caproyl lactic acid, ethanol, and polyethylene glycol-4 lauryl ether, alone or in combinations of one or more.

30. A device according to claim 29 wherein the polymeric carrier comprises an ethylene vinyl acetate copolymer.

31. A method according to claim 17 wherein the pergolide salt is provided in an amount sufficient to deliver about 1.5 to 8 mg of pergolide per day at a flux of at least about 1 μg/cm² hr.

32. A device for the transdermal administration of a pharmaceutically acceptable salt of pergolide at a therapeutically effective rate, comprising:

(a) a reservoir comprising an amount of a pharmaceutically acceptable salt of pergolide substantially free of pergolide base and a permeation enhancer selected from the group consisting of lauramide diethanolamine, monoglycerides or mixtures of monoglycerides of fatty acids, esters of $C_{10}$–$C_{20}$ fatty acids, lactate esters, caproyl lactic acid, $C_2$–$C_4$ alcohols, dimethyl lauramide, polyethylene glycol monolaurate, polyethylene glycol-4 lauryl ether, and mixtures thereof, in an amount sufficient to substantially increase the permeability of the body surface or membrane to the pergolide throughout a substantial portion of the administration period;

(b) a backing on or adjacent the body contacting-distal surface of the reservoir; and (c) means for maintaining the reservoir in drug and permeation enhancer transmitting relation with a body surface or membrane wherein the pergolide pharmaceutically acceptable salt is delivered at a therapeutically effective rate of at least about 1 μg/cm² hr for an administration period of at least 8 hours in order to administer about 1.5 to 8 mg of pergolide per day in order to provide therapeutically effective blood plasma levels of pergolide in a patient over a substantial portion of said administration period.

33. A device according to claim 32 wherein the pergolide pharmaceutically acceptable salt is present in an amount sufficient to provide said blood plasma levels of at least about 100 pg/mL.

34. A device according to claim 33 wherein the pergolide pharmaceutically acceptable salt is present in an amount sufficient to provide said blood plasma levels of about 300–1200 pg/mL.

35. A device according to claim 32 wherein the means for maintaining the reservoir in relation with the skin comprises an in-line adhesive layer on the body contacting-proximal surface of the reservoir.

36. A device according to claim 35 wherein the in-line adhesive is a polyisobutylene adhesive.

37. A method for the transdermal administration of a pharmaceutically acceptable salt of pergolide by permeation through a body surface or membrane at a therapeutically effective rate, which method comprises a) administering a pharmaceutically acceptable salt of pergolide substantially free of pergolide base to a body surface or membrane in a carrier effective to permit sustained release of the pergolide pharmaceutically acceptable salt through said body surface or membrane;

b) simultaneously coadministering a permeation-enhancing amount of a permeation enhancer selected from the group consisting of lauramide diethanolamine, monoglycerides or mixtures of monoglycerides of fatty acids, esters of $C_{10}$–$C_{20}$ fatty acids, lactate esters, caproyl lactic acid, $C_2$–$C_4$ alcohols, dimethyl lauramide, polyethylene glycol monolaurate, polyethylene glycol-4 lauryl ether, and mixtures thereof, in an amount sufficient to substantially increase the permeability of the body surface or membrane to the pergolide throughout a substantial portion of the administration period, wherein pergolide is administered at a therapeutically effective rate of at least about 1 μg/cm² hr for an administration period of at least 8 hours in order to deliver about 1.5 to 8 mg of pergolide per day in order to provide therapeutically effective blood plasma levels of pergolide in a patient over a substantial portion of said administration period.

38. A method according to claim 37 wherein said blood plasma levels are maintained at about at least 100 pg/mL.

39. A method according to claim 38 wherein said blood plasma levels are maintained at about 300–1200 pg/mL.

40. A method according to claim 37 wherein said pergolide pharmaceutically acceptable salt is delivered at a rate of at least about 30 µg/hr.

41. A device for the transdermal administration of pergolide mesylate at a therapeutically effective rate, comprising:
  (a) a reservoir comprising:
    (i) 1 to 15 wt % of pergolide mesylate sufficient to deliver about 1.5 to 8 mg of pergolide per day at a flux of at least about 1 µg/cm² hr, said reservoir substantially free of pergolide base;
    (ii) 10 to 50 wt % of a permeation enhancer selected from the group consisting of lauramide diethanolamine, monoglycerides or mixtures of monoglycerides of fatty acids, esters of $C_{10-C20}$ fatty acids, lactate esters, caproyl lactic acid, ethanol, and polyethylene glycol-4 lauryl ether, alone or in combinations of one or more;
    (iii) 35 to 85 wt % of a polymeric carrier;
  (b) a backing on or adjacent the body contacting-distal surface of the reservoir; and
  (c) means for maintaining the reservoir in drug- and permeation enhancing mixture-transmitting relation with a body surface or membrane, wherein pergolide is delivered at a therapeutically effective rate for an administration period of at least 8 hours in order to provide therapeutically effective blood plasma levels of pergolide in a patient over a substantial portion of said administration period.

42. A device for the transdermal administration of pergolide mesylate at a therapeutically effective rate, comprising:
  (a) a reservoir comprising an amount of pergolide mesylate substantially free of pergolide base and a permeation enhancer selected from the group consisting of lauramide diethanolamine, monoglycerides or mixtures of monoglycerides of fatty acids, esters of $C_{10-C20}$ fatty acids, lactate esters, caproyl lactic acid, $C_2$–$C_4$ alcohols, dimethyl lauramide, polyethylene glycol monolaurate, polyethylene glycol-4 lauryl ether, and mixtures thereof, in an amount sufficient to substantially increase the permeability of the body surface or membrane to the pergolide throughout a substantial portion of the administration period;
  (b) a backing on or adjacent the body contacting-distal surface of the reservoir; and
  (c) means for maintaining the reservoir in drug and permeation enhancer transmitting relation with a body surface or membrane wherein the pergolide mesylate is delivered at a therapeutically effective rate of at least about 1 µg/cm² hr for an administration period of at least 8 hours in order to administer about 1.5 to 8 mg of pergolide per day in order to provide therapeutically effective blood plasma levels of pergolide in a patient over a substantial portion of said administration period.

43. A device according to claim 42 wherein the permeation enhancer comprises glycerol monolaurate.

44. A device according to claim 43 wherein the polymeric carrier comprises an ethylene vinyl acetate copolymer.

45. A device according to claim 44 comprising 1 to 15 wt % of pergolide mesylate, 10 to 50 wt % of glycerol monolaurate, and 35 to 85 wt % of ethylene vinylacetate.

46. A device for the transdermal administration of pergolide mesylate at a therapeutically effective rate, comprising:
  (a) a reservoir comprising an amount of pergolide mesylate and being substantially free of pergolide base;
  (b) a backing on or adjacent the body contacting-distal surface of the reservoir; and
  (c) means for maintaining the reservoir in drug transmitting relation with a body surface or membrane wherein the pergolide is delivered at a therapeutically effective rate for an administration period of at least 8 hours in order to provide therapeutically effective blood plasma levels of pergolide in a patient over a substantial portion of said administration period.

47. A method for the transdermal administration pergolide mesylate by permeation through a body surface or membrane at a therapeutically effective rate, which method comprises administering pergolide mesylate substantially free of pergolide base to a body surface or membrane in a carrier effective to permit sustained release of the pergolide through said body surface or membrane over an administration period of at least about 8 hours in order to achieve therapeutically effective blood plasma levels of pergolide in a patient for a substantial portion of said administration period.

* * * * *